(12) United States Patent
Mason et al.

(10) Patent No.: US 6,985,764 B2
(45) Date of Patent: Jan. 10, 2006

(54) FLEX CIRCUIT SHIELDED OPTICAL SENSOR

(75) Inventors: Gene Mason, La Mirada, CA (US); Ammar Al-Ali, Tustin, CA (US); Thomas J. Gerhardt, Littleton, CO (US)

(73) Assignee: Masimo Corporation, Irvine, CA (US)

( * ) Notice: Subject to any disclaimer, the term of this patent is extended or adjusted under 35 U.S.C. 154(b) by 251 days.

(21) Appl. No.: 10/137,942

(22) Filed: May 2, 2002

(65) Prior Publication Data

US 2002/0165440 A1 Nov. 7, 2002

Related U.S. Application Data

(60) Provisional application No. 60/288,324, filed on May 3, 2001, provisional application No. 60/301,183, filed on Jun. 27, 2001.

(51) Int. Cl.
*A61B 5/00* (2006.01)
*H05K 3/02* (2006.01)

(52) U.S. Cl. .......................... 600/344; 29/846
(58) Field of Classification Search ........ 600/309–310, 600/322–323, 344, 336; 250/206, 214.1; 29/829, 846
See application file for complete search history.

(56) References Cited

U.S. PATENT DOCUMENTS

| | | | |
|---|---|---|---|
| 4,825,879 A | 5/1989 | Tan et al. |
| 4,865,038 A | 9/1989 | Rich et al. |
| 5,337,744 A | 8/1994 | Branigan |
| 5,452,717 A | 9/1995 | Branigan et al. |
| 5,482,036 A | 1/1996 | Diab et al. |
| 5,490,505 A | 2/1996 | Diab et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,678,544 A | 10/1997 | DeLonzor et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,823,950 A | 10/1998 | Diab et al. |
| 5,860,919 A | 1/1999 | Kiani-Azarbayjany et al. |
| 5,890,929 A | 4/1999 | Mills et al. |

(Continued)

FOREIGN PATENT DOCUMENTS

FR 2 685 865 A 7/1993

(Continued)

*Primary Examiner*—Eric F. Winakur
*Assistant Examiner*—Matthew J. Kremer
(74) *Attorney, Agent, or Firm*—Knobbe, Martens, Olson & Bear, LLP

(57) ABSTRACT

A flex circuit optical sensor has an integrated Faraday shield. A conductive trace layer disposed on a substrate is used to form a conductive grid which shields the face of a photodetector. A conductive ink layer is formed on a substrate side opposite the trace layer. The back and sides of the detector are shielded by flex circuit flaps that have the conductive ink layer but substantially exclude the trace layer so as to fold over and closely adhere to the detector body. The shielded substrate flaps advantageously eliminate a separate detector shield, which is typically fabricated with an etched copper part that must be attached to a flex circuit before mounting the detector.

12 Claims, 23 Drawing Sheets

U.S. PATENT DOCUMENTS

| | | |
|---|---|---|
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,014,576 A * | 1/2000 | Raley .................. 600/344 |
| 6,036,642 A | 3/2000 | Diab et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,334,065 B1 | 12/2001 | Al-Ali et al. |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 * | 5/2002 | Schulz et al. ........... 250/206 |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,725,075 B2 | 4/2004 | Al-Ali |

FOREIGN PATENT DOCUMENTS

| | | |
|---|---|---|
| WO | WO 92/21280 | 12/1992 |
| WO | WO 94 27494 A | 12/1994 |
| WO | WO 00 59374 A | 10/2000 |
| WO | WO 01/13790 A1 * | 3/2001 |

* cited by examiner

SECTION A-A

FLEX CIRCUIT SHIELDED OPTICAL SENSOR

CROSS-REFERENCE TO RELATED APPLICATIONS

This application claims a priority benefit under 35 U.S.C. § 119(e) from U.S. Provisional Patent Application Nos. 60/288,324 entitled "Pulse Oximeter Sensor Attachment Flap," filed May 3, 2001 and 60/301,183 entitled "Flex Circuit Shielded Optical Sensor," filed Jun. 27, 2001, which are both incorporated by reference herein.

BACKGROUND OF THE INVENTION

Pulse oximetry is a widely accepted noninvasive procedure for measuring the oxygen saturation level of arterial blood, an indicator of a person's oxygen supply. Early detection of low blood oxygen level is critical in the medical field, for example in critical care and surgical applications, because an insufficient supply of oxygen can result in brain damage and death in a matter of minutes. A pulse oximetry system consists of a sensor applied to a patient, a pulse oximeter, and a patient cable connecting the sensor and the pulse oximeter. The pulse oximeter may be a standalone device or may be incorporated as a module or built-in portion of a multiparameter patient monitoring system and typically provides a numerical readout of the patient's oxygen saturation, a numerical readout of pulse rate, and an audible indicator or "beep" that occurs in response to each pulse. In addition, the pulse oximeter may display the patient's plethysmograph, which provides a visual display of the patient's pulse contour and pulse rate.

SUMMARY OF THE INVENTION

One aspect of a flex circuit shielded optical sensor is an emitter and detector mounted to a flex circuit. The emitter is configured to transmit optical radiation and the detector is configured to receive optical radiation from the emitter. A plurality of flap portions of the flex circuit each having an unfolded position extending from the flex circuit and a folded position at least partially enclosing the detector. In one embodiment, the flap portions comprise a back flap configured to fold over and adhere to a first portion of the detector and a side flap configured to fold over and adhere to a second portion of the detector. In another embodiment the flex circuit comprises a substrate layer having a first side and a second side and a conductive layer disposed on the second side substantially including the flap portions so that the flap portions in the folded position shield electromagnetic interference from the detector. The sensor may also comprise a trace layer disposed on the first side providing signal connections for the detector and the emitter. A conductive grid portion of the trace layer is proximate the flap portions and is configured to form a Faraday shield for the detector in conjunction with the flap portions. The trace layer may be substantially excluded from the flap portions.

Another aspect of a flex circuit shielded optical sensor is a flex circuit substrate having a first side and an opposite second side. A trace layer is disposed on the first side and has a pattern of conductors so as to electrically connect with an emitter and a detector. A conductive grid portion of the trace layer has at least one aperture so as to pass optical radiation from the emitter to the detector. The trace layer is configured to mount the detector proximate the grid portion. In one embodiment, the at least one aperture comprises at least one hole drilled through the substrate and the grid. In another embodiment, the substrate is adapted to transmit light and the at least one aperture comprises a pattern etched in the grid. In yet another embodiment, the optical sensor further comprising a shield layer disposed on the second side. The substrate has a foldable portion including the shield layer and substantially excluding the trace layer. The foldable portion is configured to substantially enclose the detector so as to form a Faraday shield in conjunction with the conductive grid portion. The foldable portion may have a plurality of flaps adapted to adhere to the detector. In a further embodiment, the sensor further comprises a stock material retaining the substrate and having a first wrap with a first end and a second wrap with a second end, where each of the wraps is adapted for finger attachment of the substrate. The wraps are configured so that the first end is covered by the second end and the second end terminates away from a person's palm.

A further aspect of a flex circuit shielded optical sensor is an optical sensor assembly method comprising the steps of fabricating an elongated flex circuit having a component side, an opposite side and a foldable portion. Other steps are creating a plurality of traces on the component side substantially excluding the foldable portion and creating a conductive layer on the opposite side substantially including the foldable portion. Further steps are mounting a detector and an emitter to the component side, where the traces provide electrical connections for the detector and the emitter, and disposing the foldable portion around the detector so as to shield the detector from electromagnetic interference. In one embodiment, the fabricating step comprises the substep of forming a back flap and a plurality of side flaps on the foldable portion. In another embodiment, the disposing step comprises the substeps of adhering the side flaps to first portions of the detector and adhering the back flap to second portions of the detector. In a further embodiment, the assembly method also comprises the step of creating a conductive grid portion of at least one of the traces. The mounting step may comprise the substep of positioning the detector proximate the grid portion so as to shield the detector from electromagnetic interference.

Yet another aspect of a flex circuit shielded optical sensor is a substrate means for supporting a flex circuit, a trace means disposed on a first side of the substrate means for connecting to a detector and an emitter, a conductive ink means disposed on a second side of the substrate for shielding the flex circuit, and a shield means including the substrate means and the conductive ink means for folding onto and attaching to the detector. In one embodiment, the optical sensor further comprises a grid means portion of the trace means for forming a Faraday shield around the detector. The grid means may comprise an aperture means for transmitting light to the detector. In another embodiment, the optical sensor further comprises a wrap means for finger attachment without an exposed wrap end on the palm-side of a finger.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements. In addition, the first digit of each reference number indicates the figure in which the element first appears.

DETAILED DESCRIPTION OF THE PREFERRED EMBODIMENT

Sensor Configuration

Figure 1A:
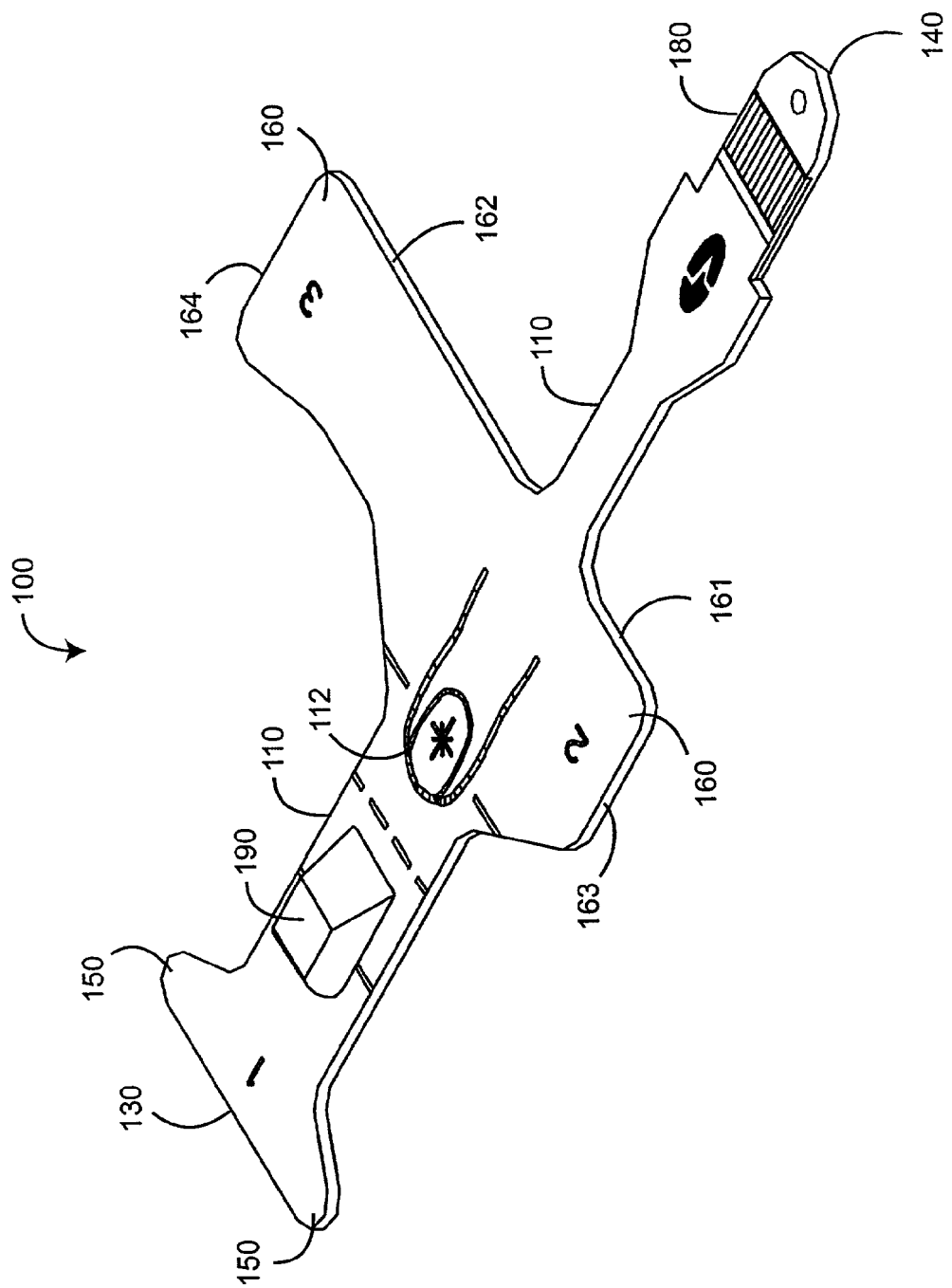
FIGS. 1A–B are perspective views of a flex-circuit-shielded optical sensor.

FIG. 1A illustrates one embodiment of a flex circuit shielded optical sensor. The sensor 100 has a central body 110, a foldover end 130, a connector end 140, a pair of adhesive end attachment wraps 150, a pair of adhesive middle attachment wraps 160, a connector 180 and a detector housing 190. The end wraps 150 and middle wraps 160 extend on either side of the central body 110 and are used to attach the sensor 100 to a patient's finger, in a manner similar to that described in U.S. Pat. No. 5,782,757 entitled "Low Noise Optical Probe," which is assigned to the assignee of the present invention and incorporated by reference herein. The central body 110 retains a flex circuit assembly 200 (FIGS. 2A–B), described in detail below. The flex circuit assembly 200 is a portion of a sensor core assembly 800 (FIG. 8A–B), which is sandwiched into a completed sensor 100, as described in detail with respect to FIGS. 8–10, below.

As shown in FIG. 1A, an emitter 760 (FIG. 7) is located proximate a printed target 112 that indicates finger placement. A detector 740 (FIG. 7) is located in the detector housing 190. The sensor 100 is configured so that, when attached to a finger, the emitter 760 (FIG. 7) projects light through the fingernail, through the blood vessels and capillaries underneath and into the detector 740 (FIG. 7), which is positioned at the finger tip opposite the fingernail. The sensor 100 may also have an identification (ID) component 780 (FIG. 7) with multiple uses depending on the manufacturer, such as an indicator of LED wavelength, sensor type or manufacturer. The connector 180 electrically connects the sensor 100 to a pulse oximetry monitor (not shown) via an associated mating connector on a patient cable (not shown).

Also shown in FIG. 1A in an unwrapped position, the middle wraps 160 include a short attachment wrap 161 and an extended attachment wrap 162. To attach the sensor to a person's finger, the short attachment wrap 161 is wrapped around the finger first. The extended attachment wrap 162 is then wrapped around the short attachment wrap 161, covering the short attachment wrap end 163. The extended attachment wrap end 164 terminates away from the person's palm, such as on the side of the finger or, for small fingers, the back-of-the-hand. In this wrapped position, there are no wrap ends 163, 164 exposed on the person's palm. As such, the wrap ends 163, 164 of the middle attachment wraps 160 are not prone to snag, attract debris or delaminate. In one embodiment, the sensor 100 has an optional extension 110 to a connector 180. Alternatively, the sensor 100 may have a connector 180 proximate the middle wraps 160 with no extension 110, such as shown in FIG. 1B, described below.

Figure 1B:
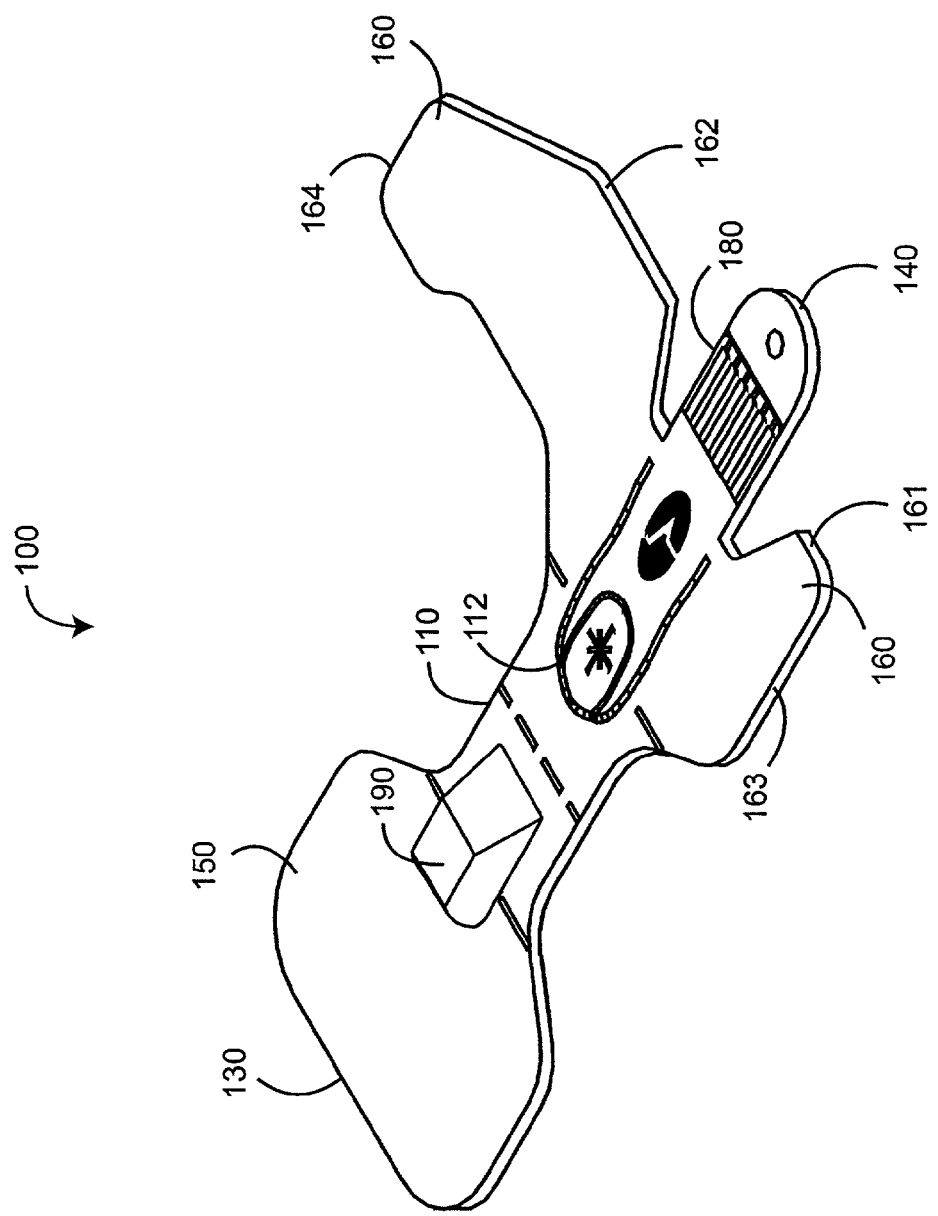

FIG. 1B illustrates another embodiment of a flex circuit shielded optical sensor. The sensor 100 has a central body 110, a printed target 112, a foldover end 130, a connector end 140, an adhesive end attachment wrap 150, a pair of adhesive middle attachment wraps 160, a connector 180 and a detector housing 190 and retains a flex circuit assembly 200 (FIGS. 2A–B), as described with respect to FIG. 1A, above. As compared with the embodiment shown in FIG. 1A, the end wrap 150 and middle wraps 160 have greater surface area to achieve better finger adhesion. In particular, the end wrap 150 is a generally rectangular, flared extension from the central body 110 having rounded corners. The middle wraps 160 include a short attachment wrap 161 and an extended attachment wrap 162. The extended attachment wrap 162 is configured to wrap around the short attachment wrap 161 so that there are no wrap ends 163, 164 exposed on the person's palm, as described with respect to FIG. 1A, above.

Figure 2A:
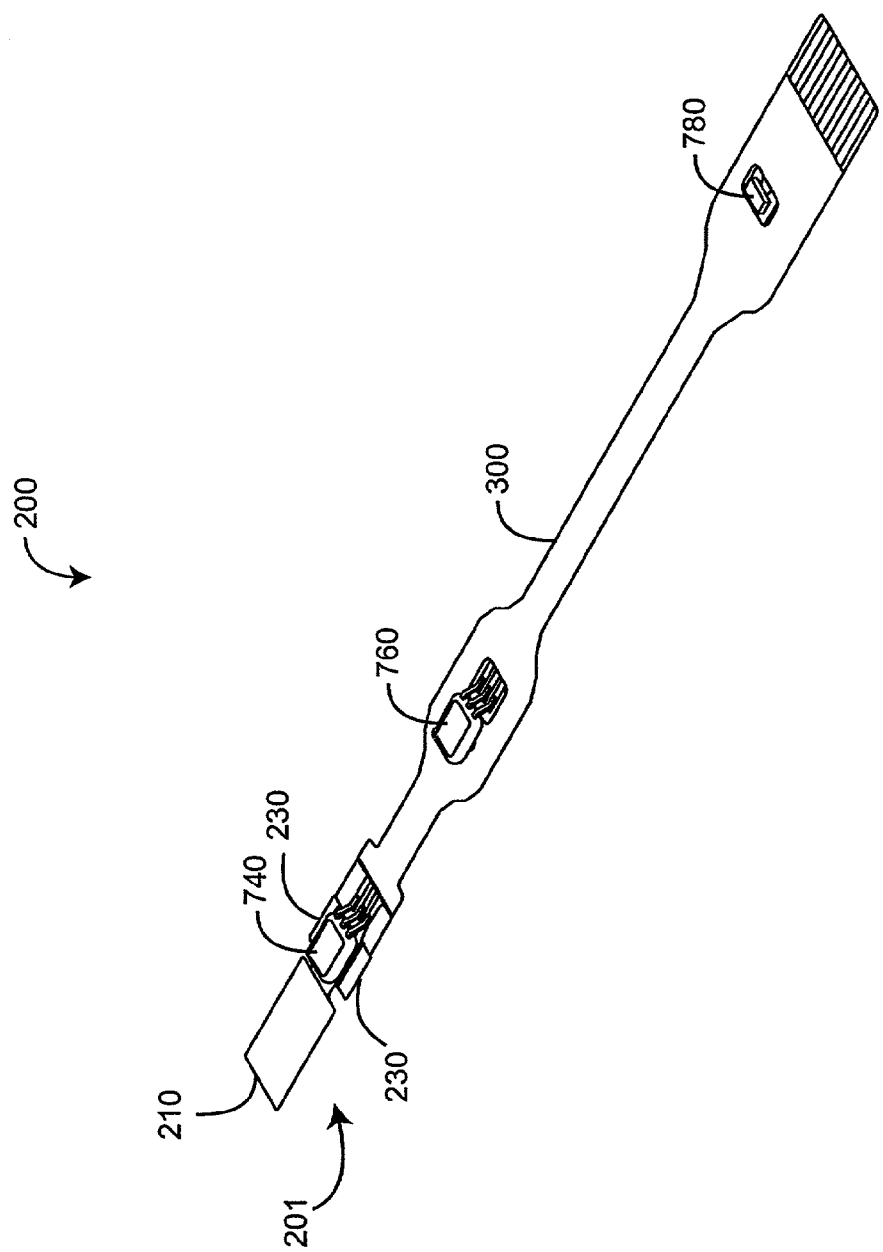
FIGS. 2A–E are perspective views of a flex circuit shield folded to enclose an optical sensor detector.

FIGS. 2A–E illustrate a flex circuit assembly 200. As shown in FIG. 2A, the flex circuit assembly 200 has a flex circuit 300, a conductive detector shield 201, a detector 740, an emitter 760, and an ID component 780. Mounted on the flex circuit 300 are the emitter 760, having both red and infrared LEDs encapsulated on a leaded carrier, the detector 740 having a photodiode encapsulated on a leaded carrier and the ID component 780 such as a resistor on a leadless carrier. The flex circuit 300 is described in detail with respect to FIGS. 3–5, below. Mounting of the components 740, 760, 780 is described in further detail with respect to FIG. 7, below.

FIGS. 2A–E also illustrate the folding of the detector shield 201 around the detector 740. As shown in FIG. 2A, the detector shield 201 is an integral portion of the flex circuit 300 and is located at one end of the flex circuit 300 proximate the detector 740. The shield 201 has a back flap 210 and a pair of side flaps 230, which have an unfolded position and a folded position. In the unfolded position illustrated in FIG. 2A, the flaps 210, 230 extend from the flex circuit 300. In the folded position illustrated in FIGS. 2D–E, each of the flaps 210, 230 at least partially enclose the detector 740.

Figure 2B:
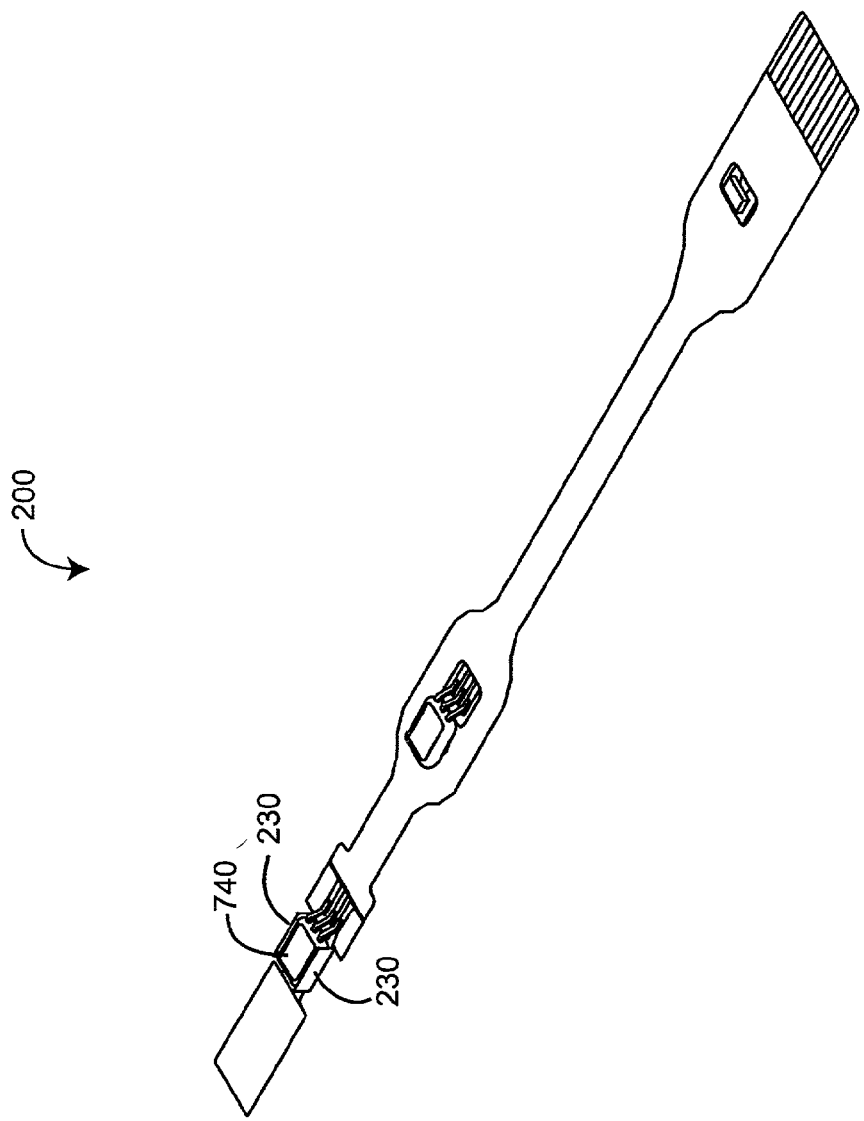
Figure 2C:
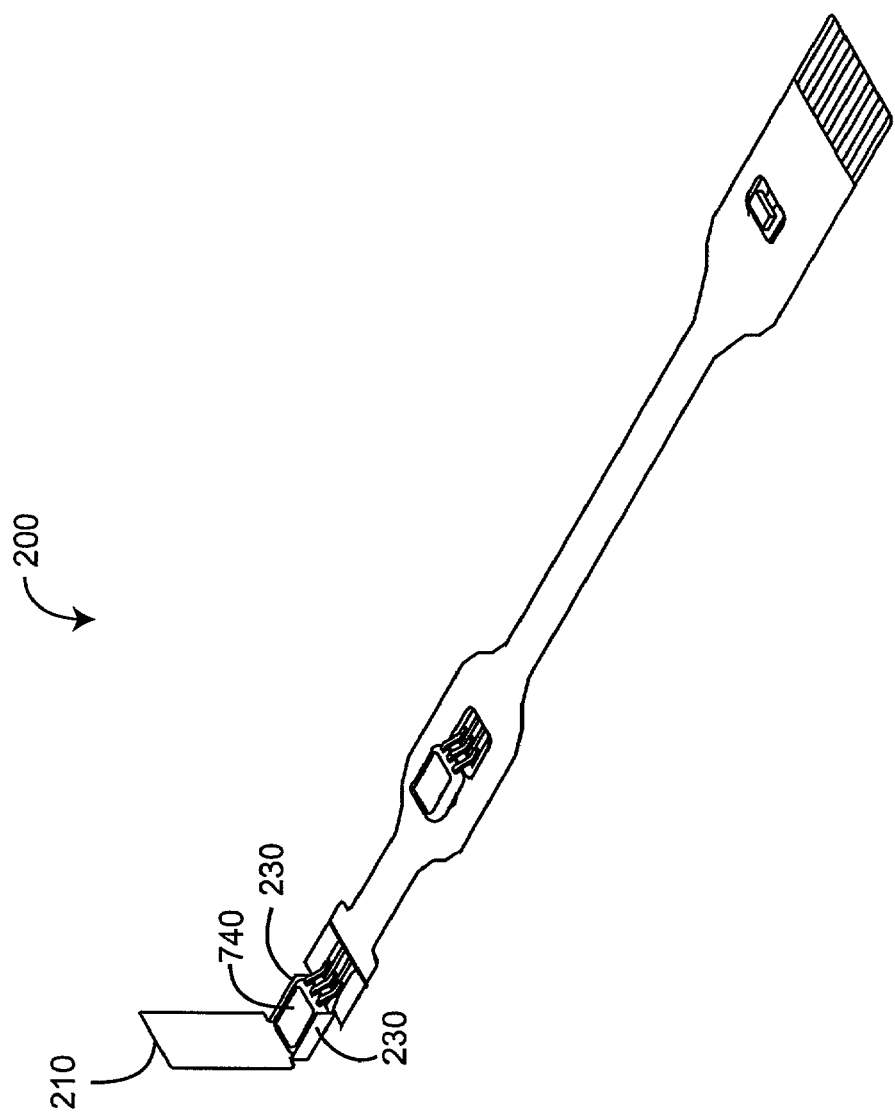
Figure 2D:
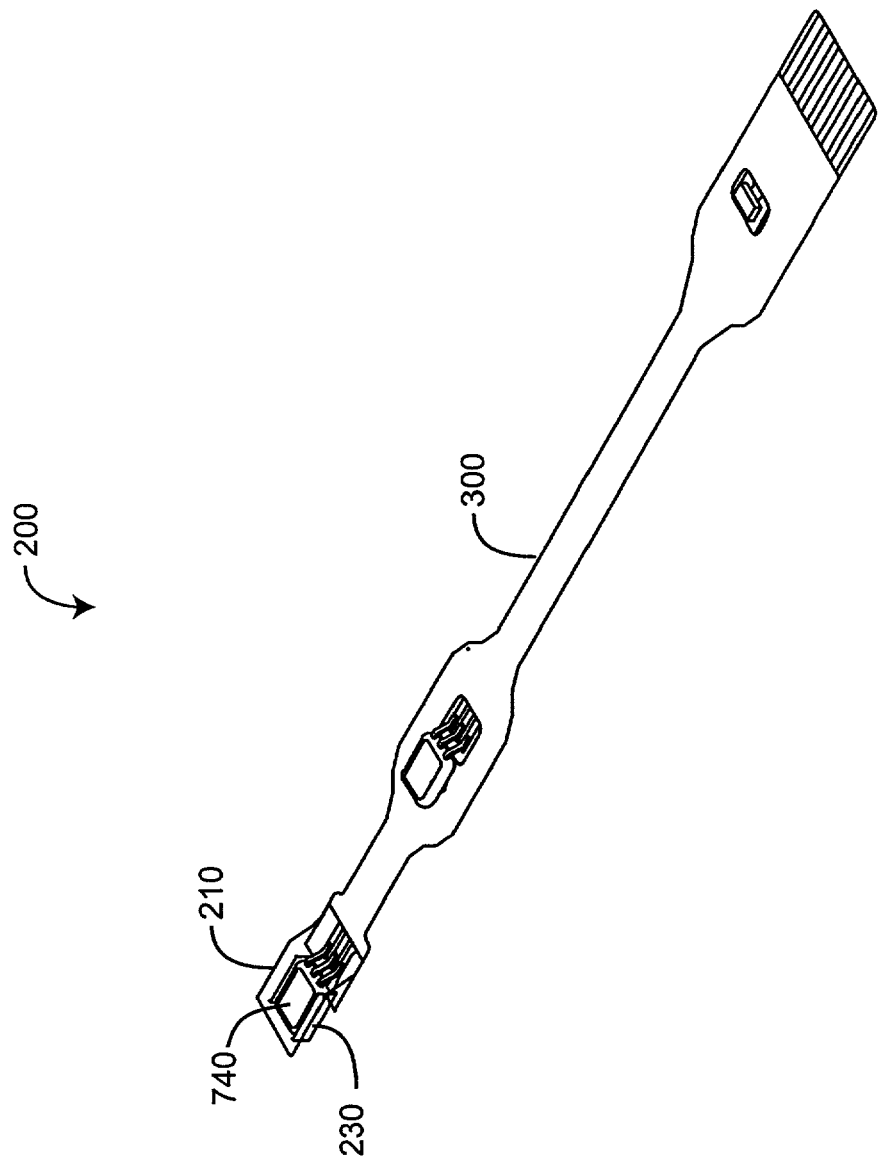
Figure 2E:
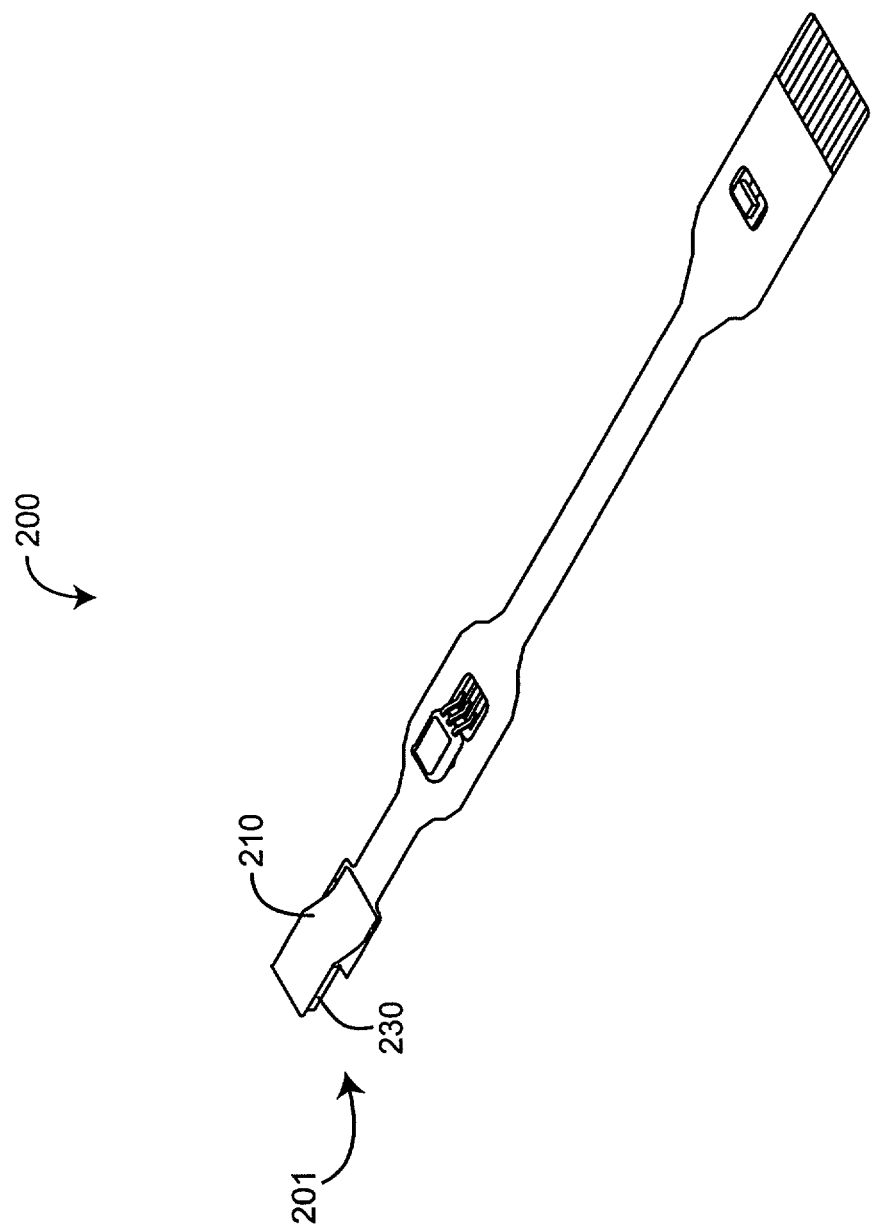

As shown in FIG. 2B, the side flaps 230 are folded toward and adhere to the sides of the detector 740. As shown in FIG. 2C, the back flap 210 is also folded toward and adheres to the top of the detector 740. As shown in FIG. 2D, the back flap 210 is also folded over the detector 740 and adheres to the back face of the detector 740 and the surface of the flex circuit 300. As shown in FIG. 2E, the detector shield 201 is configured to substantially enclose the detector 740 in conjunction with a conductive grid 310 (FIG. 3A), acting as a Faraday shield to limit electromagnetic interference (EMI) reaching the detector 740. The detector shield 201 and conductive grid 510 (FIG. 3A) are described in further detail with respect to FIGS. 3A and 5D–F, below.

Figure 3A:
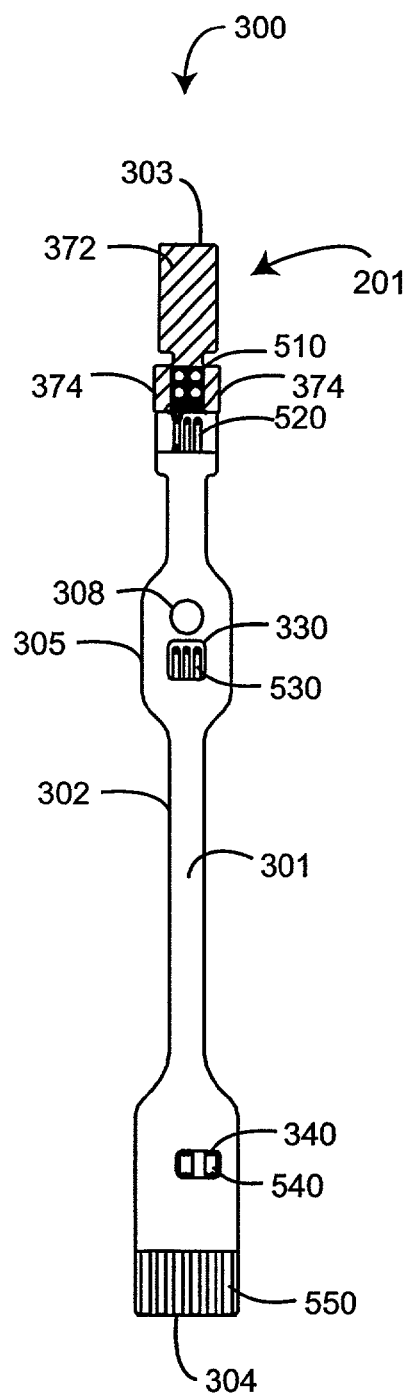
FIGS. 3A–B are component side and non-component side views, respectively, of an optical sensor flex circuit.
Figure 3B:
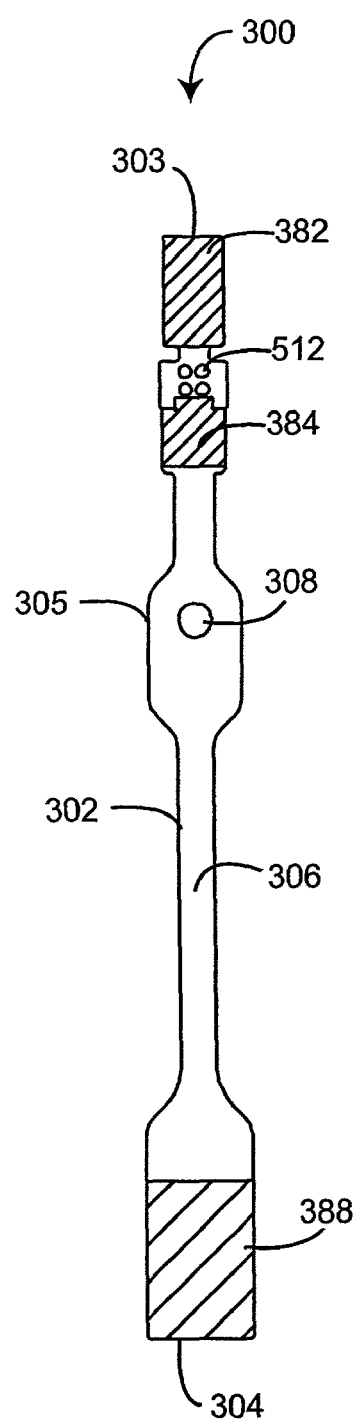

FIGS. 3A–B illustrate one embodiment of the flex circuit 300, which has an elongated body 302 widened at a connector end 304 and an opposite shield end 303. The detector shield 201, as described with respect to FIGS. 2A–E, above, is located at the shield end 303. Between the ends 303, 304 is a widened body portion 305 having an emitter aperture 308. The body 302 has a component side 301 (FIG. 3A) and a non-component side 306 (FIG. 3B). The flex circuit 300 is made up of multiple conducting and insulating layers, as described with respect to FIGS. 4–5, below.

As shown in FIG. 3A, the flex circuit component side 301 has a conductive grid 510, a detector pad 520, an emitter pad 530, an ID pad 540 and connector traces 550. The emitter pad 530 and ID pad 540 are exposed through coverlays 410, 430 (FIG. 4) at an emitter pad aperture 330 and an ID pad aperture 340, respectively. The detector 740 (FIG. 7), emitter 760 (FIG. 7) and ID 780 (FIG. 7) components are mounted to the flex circuit 300 at the detector 520, emitter 530 and ID 540 pads, as described with respect to FIG. 7, below. The detector shield 201 has a back flap pressure sensitive adhesive (PSA) 372 and a side flap PSA 374 that allow the shield 201 to adhere to the detector 740 (FIG. 7), as described with respect to FIGS. 2A–E, above.

Figure 7:
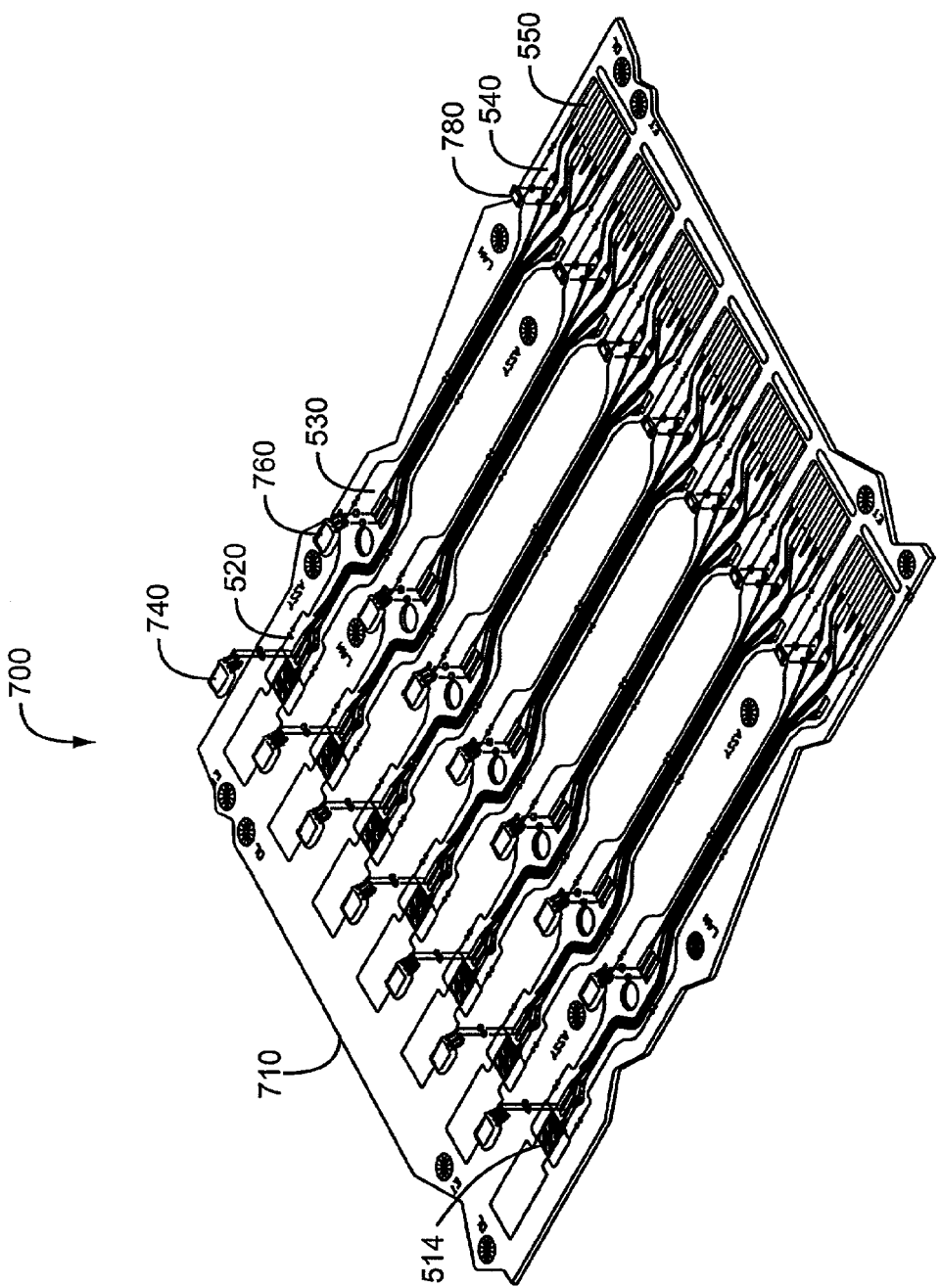
FIG. 7 is a component-side perspective view of a flex circuit panel.

As shown in FIG. 3B, the non-component side 306 has a cover PSA 382 and a cavity PSA 384 that adhere inside the detector housing 190 (FIG. 1) and also a tab PSA 388 that adheres to the connector tab 820 (FIG. 8A), as described with respect to FIGS. 8A–B, below. The conductive grid 510 (FIG. 3A) has apertures 512 that allow light to reach the detector 740 (FIG. 7). Specifically, light is transmitted from the emitter component 760 (FIG. 2A), through the emitter aperture 308, through a fingernail bed and exits from a fingertip, entering the detector housing 190 (FIG. 1) and into the detector grid 510 to be received by the detector 740 (FIG. 7). The flex circuit 300 has printed traces of deposited or etched conductive material, described with respect to FIG. 5D, below.

Figure 4:
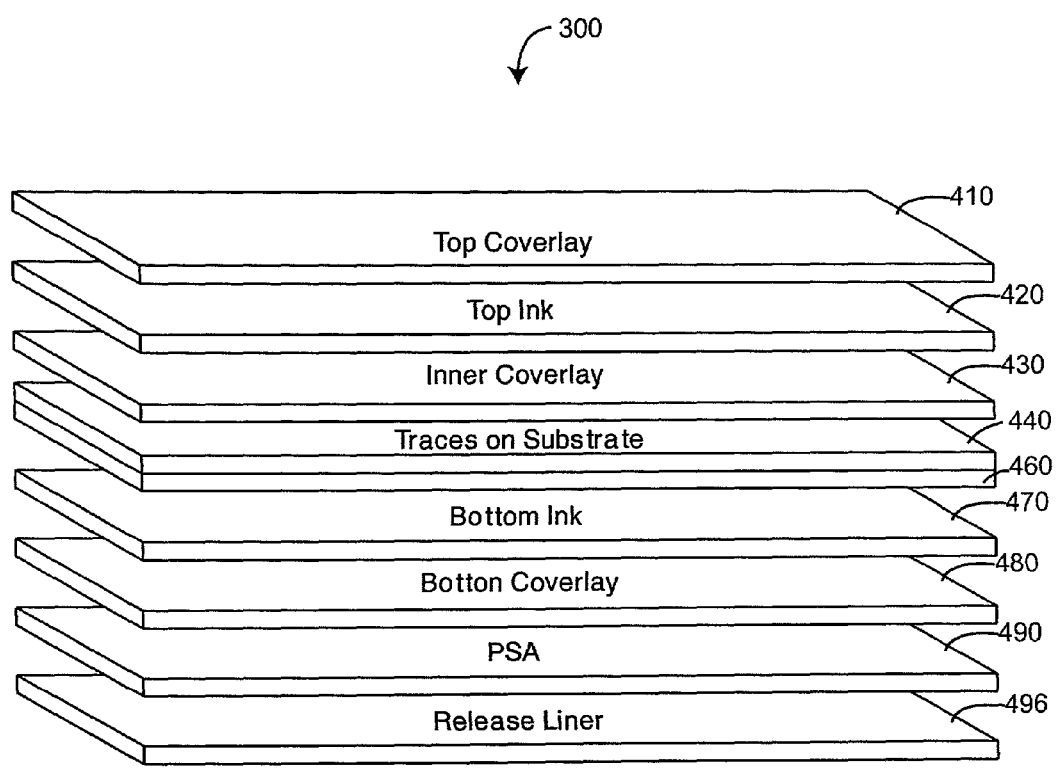
FIG. 4 is a graphical depiction identifying the relative placement of various flex circuit layers.

FIG. 4 illustrates the layered structure of the flex circuit 300, which includes a top coverlay 410, a top ink layer 420, an inner coverlay 430, a trace layer 440 and a substrate layer 460, a bottom ink layer 470, a bottom coverlay 480, a PSA layer 490 and a release liner 496. The trace layer 440 consists of conductive material carried on an insulating substrate 460. The trace layer 440 has a trace pattern that defines a conductive grid 510, a detector pad 520, an emitter pad 530, an ID pad 540, connector contacts 550 and associated interconnects. In a particular embodiment, the trace layer 440 and substrate layer 460 are constructed from a single sided 1 oz. rolled/annealed copper clad 1 mil. polyimide film, and a trace pattern is etched from the copper accordingly. The bottom ink layer 470 is carried on the opposite side of the insulating substrate 460, and, in a particular embodiment, is DUPONT CB028 silver-filled thermoplastic screenable ink. The inner coverlay 430 carries the top ink layer 420 and insulates it from the trace layer 440. Thru-holes in the inner coverlay 430 and substrate 460 provide selective connections between trace layer 440, the top ink layer 420, and the bottom ink layer 470. The top coverlay 410 and bottom coverlay 480 provide insulating protection for the top ink layer 420 and the bottom ink layer 470. The PSA layer 490 and the release liner layer 496 provide the cover, cavity and tab PSA 382, 384, 388 (FIG. 3B). Similar layers (not shown) on the top coverlay 410 provide the detector shield PSA 372, 374 (FIG. 3A). In a particular embodiment, the coverlays 410, 430, 480 are 1 mil polyimide and the PSA is 3M-467MP. These layers 410–470 are described in further detail with respect to FIGS. 5A–F, below.

Figure 5A:
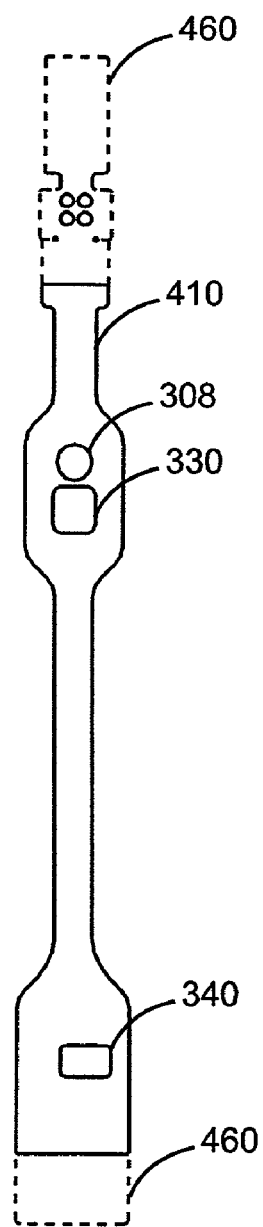
FIGS. 5A–F are views of the various flex circuit layers.

FIGS. 5A–F illustrate the flex circuit layers identified with respect to FIG. 4, above. FIG. 5A illustrates the top coverlay 410 positioned relative to the substrate 460 (dashed outline). The top coverlay 410 is an insulating film having an emitter aperture 308, an emitter pad aperture 330 and an ID pad aperture 340. The emitter aperture 330 allows light from the emitter 760 (FIG. 7) to pass through the coverlay 410 and other layers. The emitter pad aperture 330 and ID pad aperture 340 expose the emitter pad contacts 530 (FIG. 3A) and ID pad contacts 540 (FIG. 3A) for attachment of the emitter 760 (FIG. 7) and ID component 780 (FIG. 7). In one embodiment, the top coverlay 410 is 1 mil polyimide.

Figure 5B:
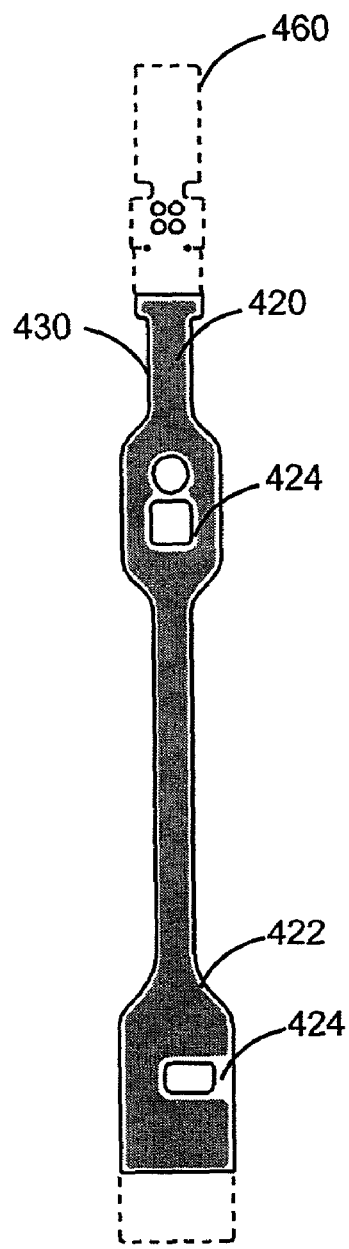
Figure 5C:
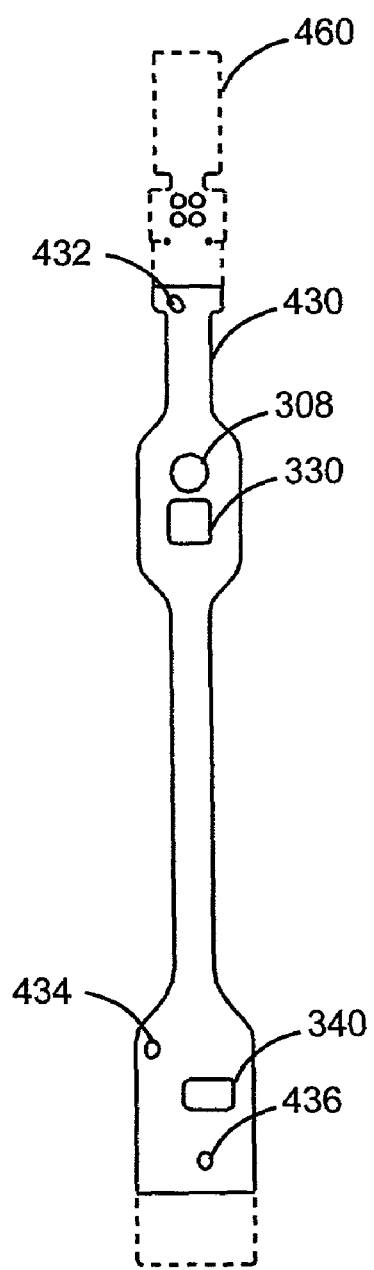

FIG. 5B illustrates the top ink layer 420 positioned relative to the substrate 460 (dashed outline) and the inner coverlay 430 (solid outline). The top ink layer 420 (filled area) is applied to the inner coverlay 430 with a pull back 422 around the periphery of the inner coverlay 430. Additional pullbacks 424 are around the peripheries of the emitter aperture 308 (FIG. 5C), the emitter pad aperture 330 (FIG. 5C) and the ID pad aperture 340 (FIG. 5C). In one embodiment, the top ink layer is DUPONT CB028 silver-filled thermoplastic screenable ink and the pullbacks 422, 424 are a minimum 25 mil.

Figure 5D:
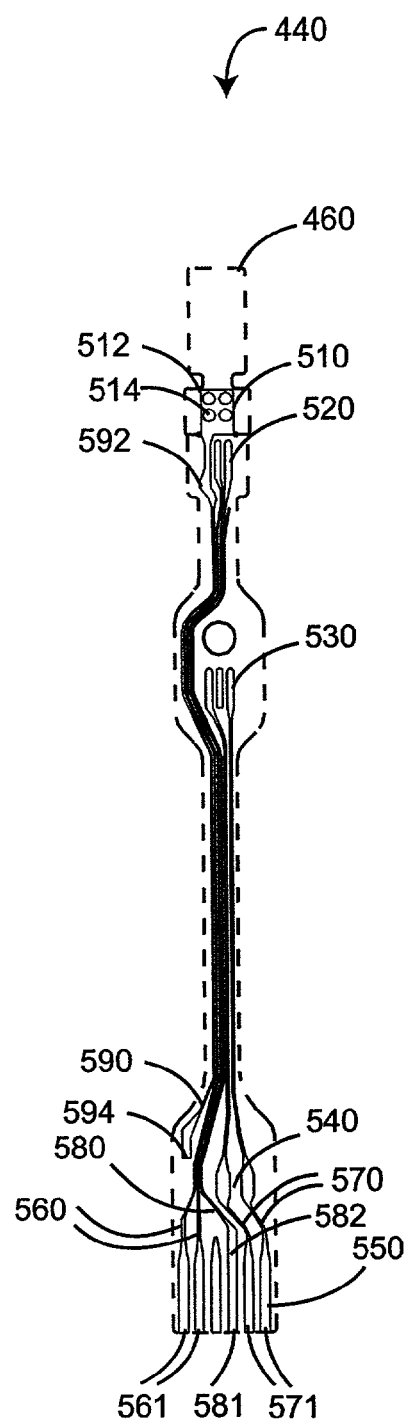

FIG. 5C illustrates the inner coverlay 430 positioned relative to the substrate 460 (dashed outline). The inner coverlay 430 is an insulating film having an emitter aperture 308, an emitter pad aperture 330 and an ID pad aperture 340, corresponding to those described with respect to the top coverlay 410 (FIG. 5A), above. The inner coverlay 430 has thru-holes 432, 434, 436 that allow the top ink layer 420 (FIG. 5B) to electrically connect with portions of the trace layer 440 (FIG. 5D). In particular, an upper thru-hole 432 and a middle thru-hole 434 provide connections to a grid trace 590 (FIG. 5D), and a lower thru-hole 436 provides a connection to a guard trace 580 (FIG. 5D).

FIG. 5D illustrates the trace layer 440 positioned relative to the substrate 460 (dashed outline). The trace layer 440 is advantageously substantially excluded from the flap portions 461, 465 (FIG. 5E) of the substrate layer 460, allowing the flaps 210, 230 (FIGS. 2A–E) to fold over and closely adhere to the detector 740 (FIGS. 2A–E) without obstruction from circuit components, conductors and connectors. The trace layer 440 has a detector grid 510, a detector pad 520, an emitter pad 530, an ID pad 540, and connector contacts 550. The grid 510 has a grid conductor 512 that provides an EMI shield for the detector 740 (FIG. 7) in conjunction with the flex circuit shield 201 (FIG. 3A). The grid 510 also has grid apertures 514 that allow light to reach the detector 740 (FIG. 7). Detector traces 560 electrically connect a detector pinout portion 561 of the contacts 550 to the detector pad 520. Emitter traces 570 electrically connect an emitter pinout portion 571 of the contacts 550 to the ID pad 540 and the emitter pad 530. A guard trace 580 extends from a shield pinout portion 581 of the contacts 550 proximate the detector traces 560 to a stub proximate the detector pad 520. A grid trace 590 extends from the grid 510 to a stub proximate the connector contacts 550. Grid pads 592, 594 provide an electrical connection via thru-holes 432, 434 (FIG. 5C) and thru-holes 462, 464 (FIG. 5E) at either end of the grid trace 590 to the top ink layer 420 (FIG. 5B) and bottom ink layer 470 (FIG. 5F). A guard pad 582 provides for an electrical connection via a thru-hole 436 (FIG. 5C) and a thru-hole 466

(FIG. 5E) at one end of the guard trace 580 to the top ink layer 420 (FIG. 5B) and bottom ink layer 470 (FIG. 5F), respectively.

Figure 5E:
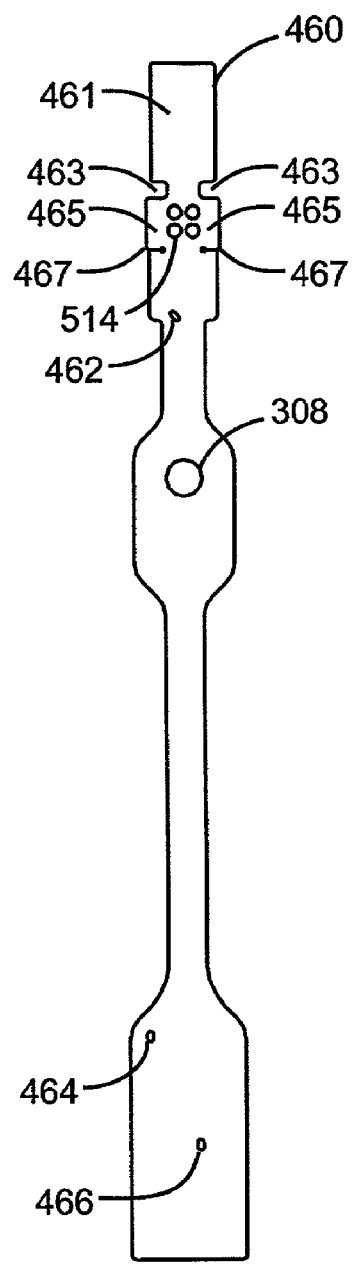
Figure 5F:
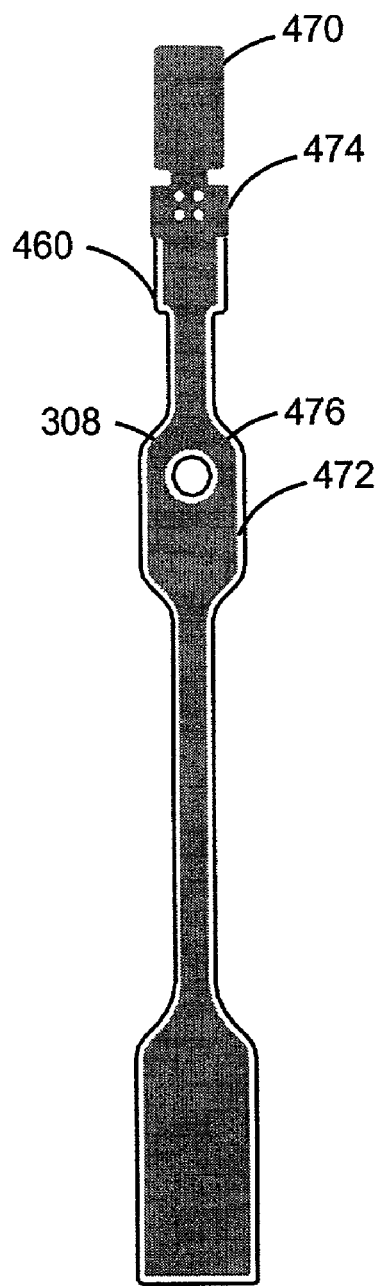

FIG. 5E illustrates the substrate layer 460, which has back flap 461 and side flaps 465 that are the substrate layer portions of the shield back flap 210 (FIGS. 2A–E) and side flaps 230 (FIGS. 2A–E), respectively. The substrate layer 460 also has indents 463 that narrow the substrate between the back flap 461 and the side flaps 463, allowing the back flap 461 to fold as described with respect to FIGS. 2A–E, above. Further, the substrate layer 460 has slots 467 on the opposite end of the side flaps 465 from the indents 463 that, in conjunction with the indents 463 allow the side flaps 465 to fold as described with respect to FIGS. 2A–E, above. In addition, the substrate layer 460 has grid apertures 514 and an emitter aperture 308, described with respect to FIGS. 3A–B, above. Substrate thru-holes 462, 464, 466 are drilled to allow the bottom ink 470 (FIG. 5F) to connect with portions of the trace layer 440 (FIG. 5D), as described above.

FIG. 5F illustrates the bottom ink layer 470 positioned relative to the substrate 460 (solid outline). The bottom ink layer 470 is advantageously substantially included on the flap portions 461, 465 (FIG. 5E) of the substrate layer 460, allowing the flaps 210, 230 (FIG. 2A–E) to shield the detector 740 (FIGS. 2A–E) from electromagnetic interference. The bottom ink layer 470 (filled area) is applied to the substrate 460 with a pull back 472 around the periphery of the substrate 460 except in a shield area 474 proximate the detector end of the substrate. The bottom ink layer 470 also has a pull back 476 around the emitter aperture 308. In one embodiment, the bottom ink layer is DUPONT CB028 silver-filled thermoplastic screenable ink and the pullback is a minimum 25 mil.

Sensor Fabrication

Flex Circuit Assembly

Figure 6:
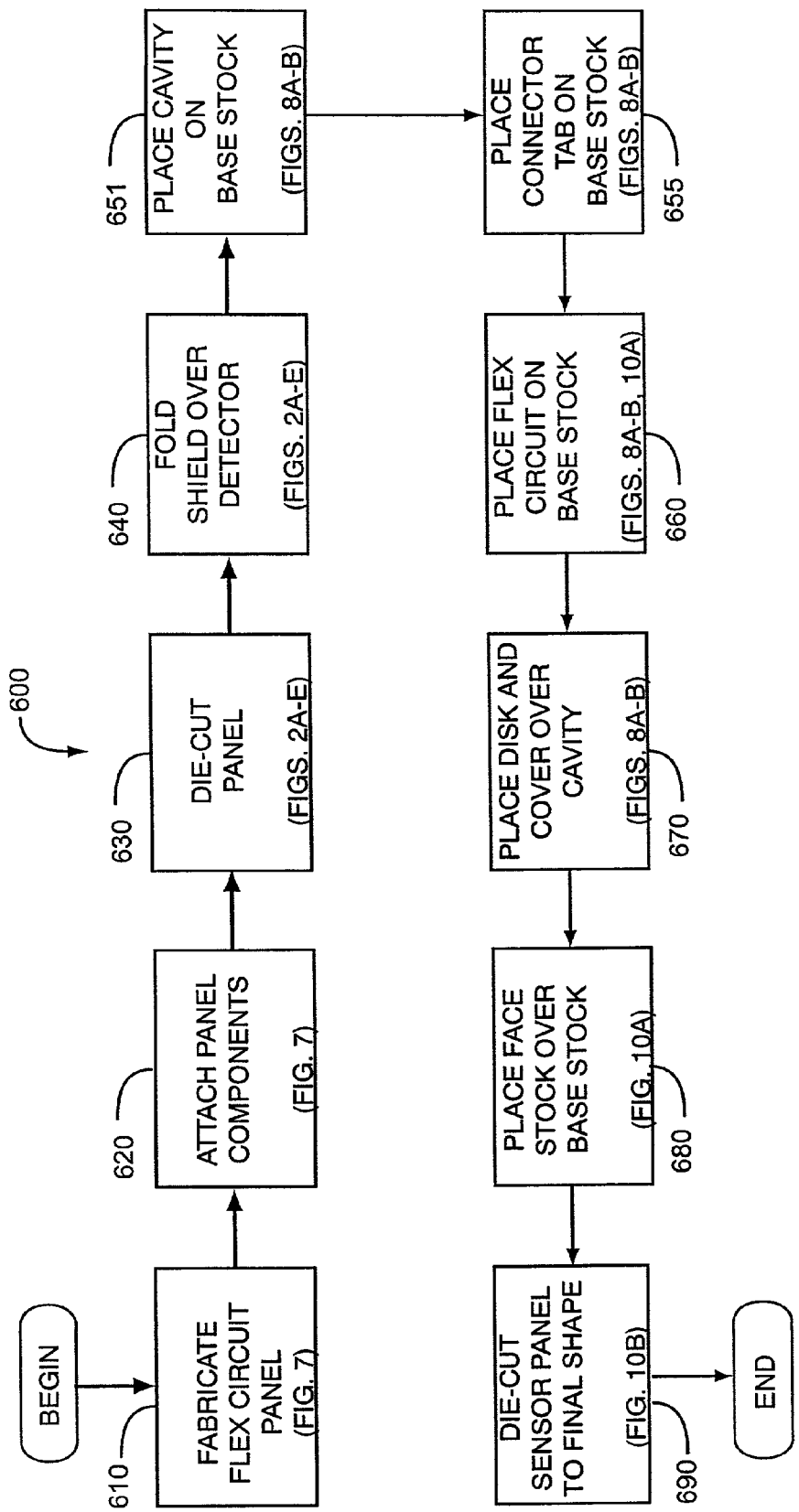
FIG. 6 is a functional flowchart of flex circuit shielded optical sensor construction.

FIG. 6 illustrates general construction steps 600 for a flex-circuit-shielded optical sensor 100 (FIG. 1). As represented by a fabricate flex circuit panel activity block 610, multiple flex circuits 300 (FIGS. 3A–B) are formed on a panel constructed of multiple layers 400 (FIG. 4), as described above. In a particular embodiment, a 7-up panel layout is used. Represented by an attach panel components activity block 620, panel components are attached to each of the multiple flex circuits on a panel 700 (FIG. 7).

FIG. 7 illustrates the flex-circuit panel fabrication and panel component attachment. Multiple flex circuits are formed by etching a pattern of conductors in the trace layer 440 (FIG. 4), which creates a circuit as described with respect to FIG. 5D, above. Thru-holes are drilled in the inner coverlay 430 (FIG. 4) and substrate 460 (FIG. 4), as described with respect to FIGS. 5C, 5E, above. The inner coverlay 430 (FIG. 4) and substrate 460 (FIG. 4) layers are laminated. Conductive ink is screened onto the inner coverlay 430 (FIG. 4) and substrate 460 (FIG. 4) as described with respect to FIGS. 5B and 5F, above. The remaining layers are laminated. The contacts 550 are selectively electroplated with gold. In a particular embodiment, the plating is 10 micro inches minimum of hard gold using a pulse plating method over 75±25 micro inches of nickel. Grid aperture holes 514 are drilled. The detector 740, emitter 760 and ID 780 components are electrically connected to the panel pads 520, 530, 540.

As shown in FIG. 6, represented by a die-cut panel activity block 630, the flex circuit panel 700 (FIG. 7), described above, is die-cut to separate individual flex circuits 200 (FIGS. 2A–E). Represented by a fold shield over detector activity block 640 the shield 201 of each flex circuit assembly 200 is folded so as to enclose the detector 740 (FIG. 7) and shield it from EMI, as described with respect to FIGS. 2A–E, above.

Sensor Core Assembly

Figure 8A:
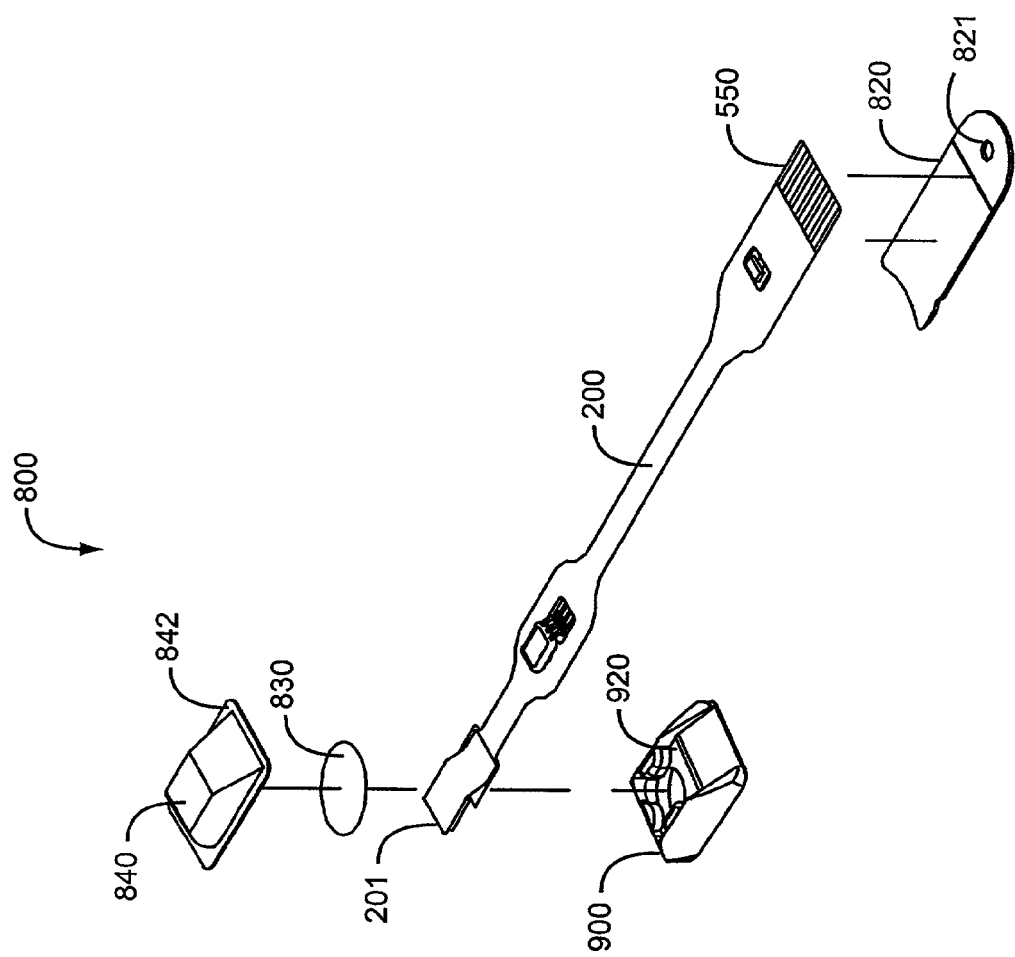
FIGS. 8A–B are exploded and assembled perspective views, respectively, of a sensor core assembly.

Also shown in FIG. 6, a place cavity on base stock activity block 651, a place connector tab on base stock activity block 655 and a place flex circuit on base stock activity block 660 represent attachment of the detector cavity 900 (FIG. 9) and the connector tab 820 (FIG. 8A) to the flex circuit assembly 200 (FIG. 8A). A place disk and cover over cavity activity block 670 represents completing the detector housing 190 (FIG. 8B) to finish a sensor core assembly 800 (FIG. 8A–B) as described below.

Figure 8B:
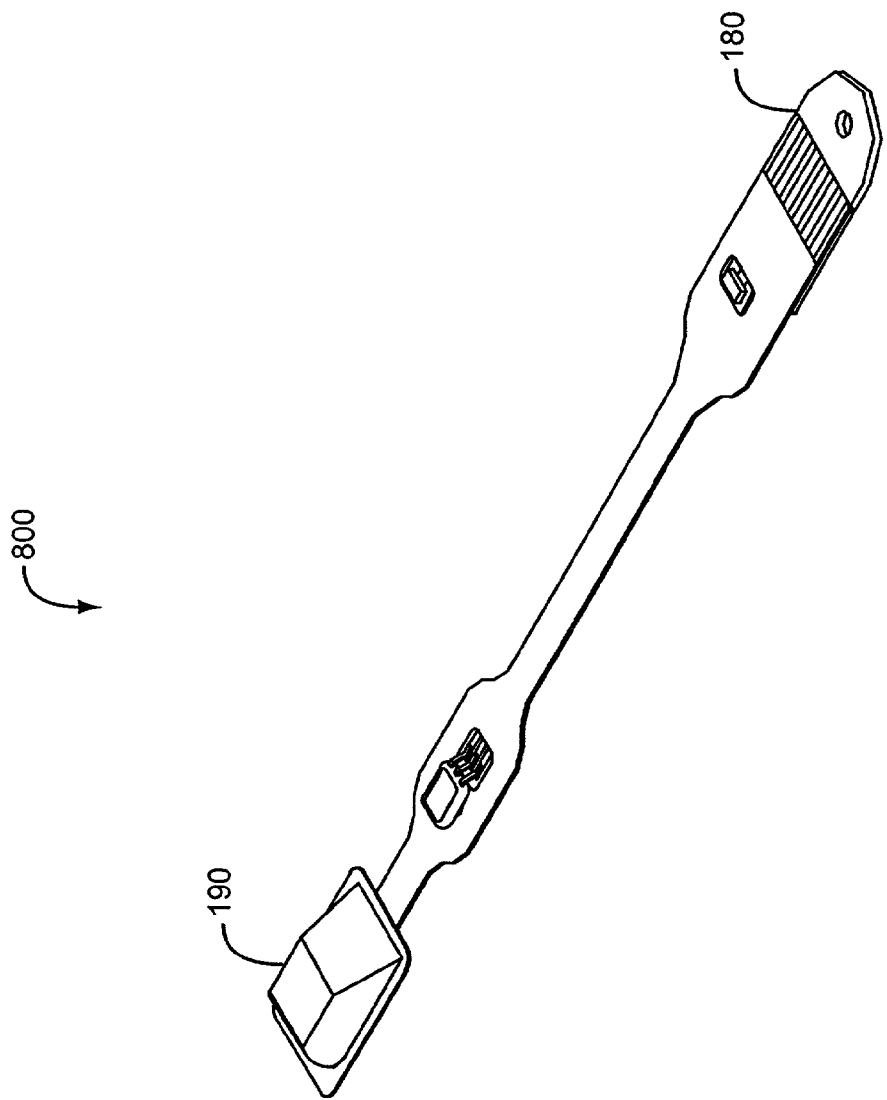
Figure 9A:
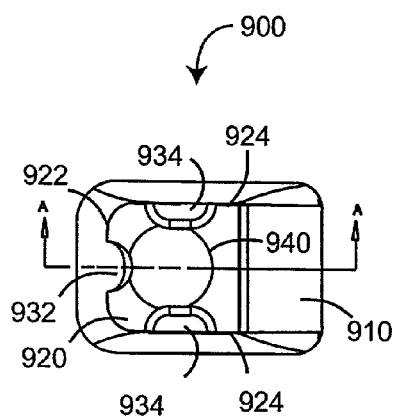
FIG. 9A–E are top, sectional, bottom, front and perspective views, respectively, of a detector cavity.
Figure 9D:
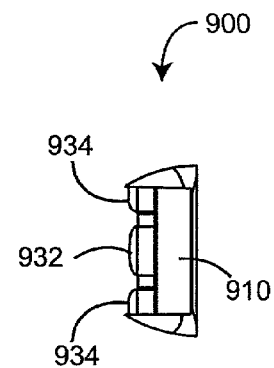
Figure 9B:
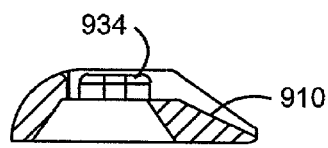
Figure 9C:
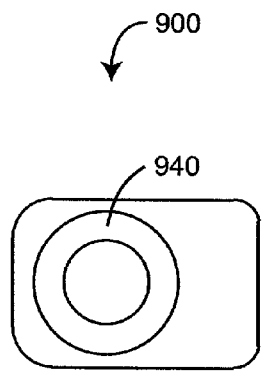
Figure 9E:
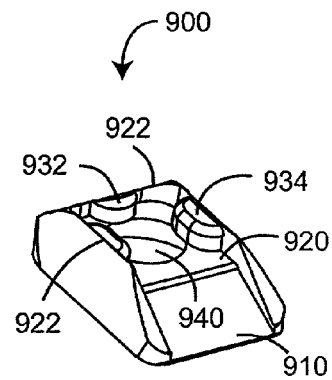

FIGS. 8A–B illustrate the sensor core assembly 800, which has a flex circuit assembly 200, including a folded over flex circuit detector shield 201, as described with respect to FIGS. 2A–E and 7, above. The sensor core assembly 800 also has a connector tab 820, a detector cavity 900, an opaque optical disk 830 and a cover 840. The connector tab 820 attaches with tab PSA 388 (FIG. 3B) behind the connector contacts 550, forming a connector plug 180 configured to engage and electrically connect with a patient cable connector socket (not shown) as described in U.S. Pat. No. 5,782,757, referenced above. The connector tab 820 has an aperture 821 that catches onto a latching portion of the mating socket. In a particular embodiment, the connector tab 820 is fabricated of an ABS polymer blend.

As shown in FIGS. 8A–B, the cavity 900, disk 830 and cover 840 form a detector housing 190 that retains the detector 740 (FIG. 7) and corresponding flex circuit shield 201. The cavity 900 provides a receptacle 920 for the shielded detector 740 (FIG. 7) and secures the shield 201 against the detector 740 (FIG. 7), as described with respect to FIGS. 9A–E, below. Cavity PSA 384 (FIG. 3B) adheres a portion of the flex circuit assembly 200 inside the cavity 900. The cover 840 fits over the cavity 900 to physically retain the detector 740 (FIG. 7) and to seal out ambient light. An opaque disk 830 provides further ambient light protection and, in one embodiment, is a metal foil. Cover PSA 382 (FIG. 3B) adheres the disk 830 and cover 840 to the flex circuit assembly 200. The cover 840 has a flange 842 that serves as a bonding surface for base stock 1010 (FIG. 10A) and face stock 1020 (FIG. 10A) material. In one embodiment, the cover 840 is vacuum formed from polystyrene and has an opaque characteristic obtained from coating or from its construction material.

FIGS. 9A–E illustrate a detector cavity 900, which has a ramp 910, a rectangular receptacle 920, alignment guides comprising a back guide 932 and two side guides 934 and a cavity aperture 940. The rectangular receptacle 920 is adapted to receive the detector end of the flex circuit assembly 200 (FIGS. 8A–B). The ramp 910 is wedge-shaped and provides for a smooth transition for the flex circuit assembly 200 (FIGS. 8A–B) between the surface of the base stock 1010 (FIG. 10A) and the surface of the rectangular receptacle 920. The alignment guides 932, 934 hold the flex circuit assembly 200 (FIGS. 8A–B) in position so that the detector 740 (FIG. 7) aligns properly with the aperture 940. Also, the back guide 932 secures the back flap 210 (FIGS. 2A–E) and the side guides 934 secure the side flaps 230 (FIGS. 2A–E) against the detector 740 (FIGS. 2A–E). The aperture 940 stabilizes a finger within the sensor so as to reduce optical decoupling between the emitter and the detector, avoids compression of finger tissue so as to stabilize the optical path length through the finger, and reduces light-piping, i.e. direct coupling of light between the detector 740 (FIG. 7) and emitter 760 (FIG. 7), as described with respect to U.S. Pat. No. 5,782,757, referenced above. In one embodiment, the cavity 900 is made from an ABS polymer blend and has an opaque characteristic obtained from coating or from its construction material. In a particular embodiment, the aperture 940 is conical or cylindrical in shape.

Sensor Panel Assembly

Further shown in FIG. 6, represented by a place face stock over base stock activity block 680, the face stock 1020 (FIG. 10A) placement over the base stock 1010 (FIG. 10A) retains the sensor assembly 800 (FIG. 8B) within the stock material, as described with respect to FIGS. 10A–B, below. As represented by a die-cut sensor panel to final shape activity block 690, individual sensors 100 (FIG. 10B) are cut from the sensor panel 1000 (FIGS. 10A–B), as described below. In a particular embodiment, the sensor panel 1000 (FIGS. 10A–B) is configured for two sensors 100 (FIG. 10B).

Figure 10A:
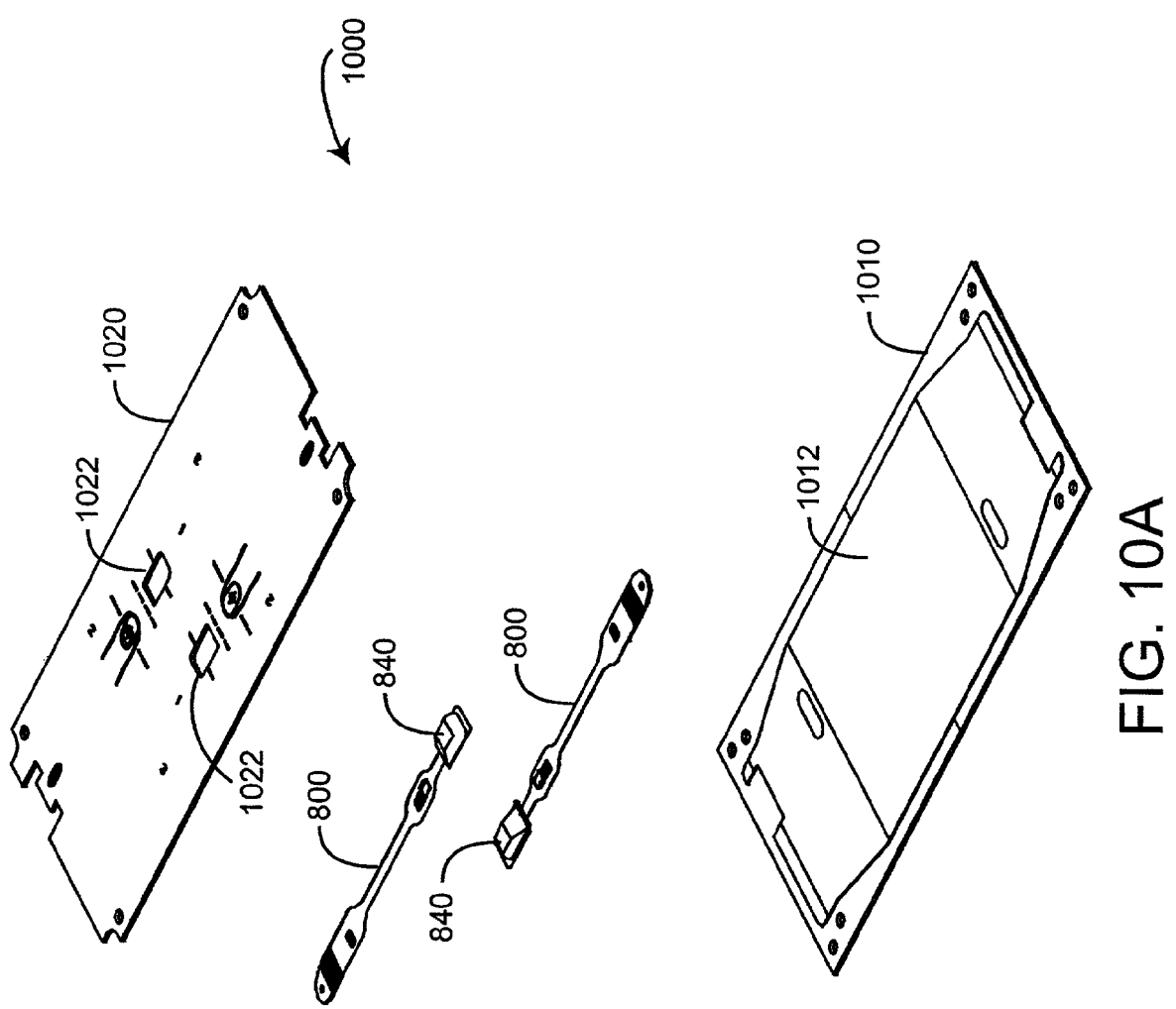
FIGS. 10A–B are an exploded view and a perspective view, respectively, of a sensor panel.
Figure 10B:
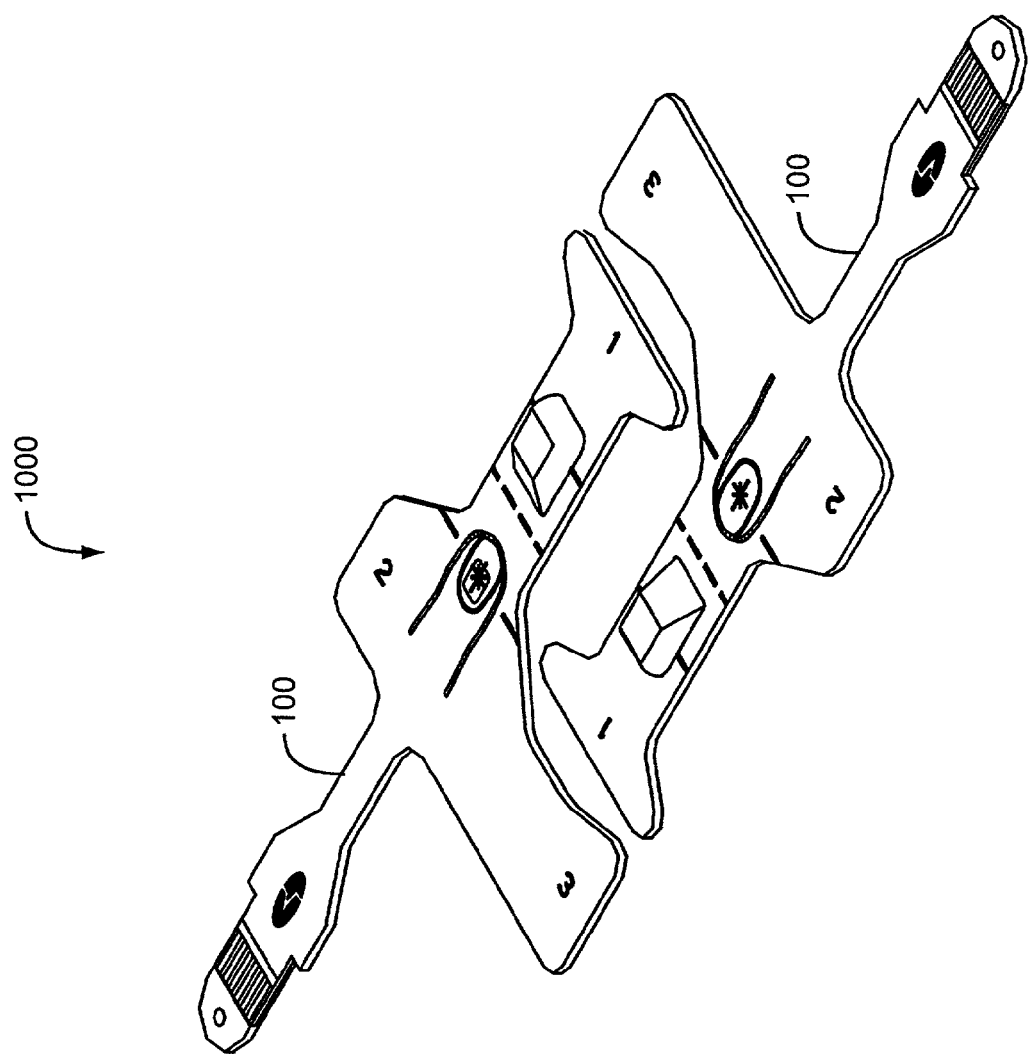

FIGS. 10A–B illustrate a sensor panel 1000, which has a base stock 1010 and a face stock 1020 enclosing multiple sensor core assemblies 800. As shown in FIG. 10A, the base stock 1010 is a flexible material that is transparent to the wavelength of the emitter. In an alternative embodiment, the base stock 1010 has holes corresponding to the emitter apertures 308 (FIGS. 3A–B) and grid apertures 514 (FIG. 5E) of the sensor core assemblies 800. The base stock 1010 has PSA on the base stock side 1012 to which the face stock 1020 is applied. In one embodiment, the face stock 1020 is a flexible woven material, such as Betham part no. 1107S. The face stock 1020 has housing apertures 1022 that allow portions of the detector housing covers 840 to protrude through the face stock 1020. In one embodiment, the face stock 1020 has PSA on the side (not visible) facing the base stock 1010. A sensor panel 1000 is created by sandwiching the sensor core assemblies 800 between the base stock 1010 and the face stock 1020 and applying pressure so that the base stock 1010 and face stock 1020 bond together, retaining the sensor core assemblies 800.

As shown in FIG. 10B, the assembled sensor panel 1000 is cut and the excess material discarded to complete multiple sensors 100. In one embodiment, a completed sensor panel assembly 1000 forms two sensors 100.

The flex circuit shielded optical sensor has been disclosed above with respect to a polyimide substrate supporting a copper trace layer. A detector Faraday shield has a detector grid portion fabricated from the copper trace layer and aperture holes drilled through the substrate and the grid so as to allow light to be received by the detector. In an alternative embodiment, a polyester nitrile (PEN) substate supports the copper trace layer. The grid has an aperture pattern etched in the trace layer rather than drilled aperture holes. The PEN material is clear, allowing light to pass to the detector while maintaining mechanical strength in the grid area.

Although the flex circuit shielded optical sensor has been described in terms of certain preferred embodiments, other embodiments will be apparent to those of ordinary skill in the art from the disclosure herein. Moreover, these embodiments are disclosed by way of examples only and are not to limit the scope of the claims that follow. One of ordinary skill in the art will appreciate many variations and modifications.

Additionally, all publications, patents, and patent applications mentioned in this specification are herein incorporated by reference to the same extent as if each individual publication, patent, or patent application was specifically and individually indicated to be incorporated by reference.

What is claimed is:

1. An optical sensor comprising:
    a flex circuit substrate having a first side and an opposite second side;
    a trace layer disposed on said first side having a pattern of conductors so as to electrically connect with an emitter and a detector,
    a conductive grid portion of said trace layer having at least one aperture so as to pass optical radiation from said emitter to said detector, said trace layer configured to mount said detector proximate said grid portion;
    a shield layer disposed on said second side, said substrate having a plurality of foldable portions including said shield layer and substantially excluding said trace layer, said plurality of foldable portions being configured to substantially enclose said detector so as to form a Faraday shield in conjunction with said conductive grid portion.

2. The optical sensor according to claim 1 wherein said plurality of foldable portions comprise a plurality of flaps adapted to adhere to said detector.

3. The optical sensor according to claim 1 further comprising:
    a stock material retaining said substrate and having a first wrap with a first end and a second wrap with a second end,
    each of said wraps adapted for finger attachment of said substrate,
    said wraps configured so that, in a wrapped position, said first end covers said second end and said second end terminates distal to a person's palm.

4. An optical sensor assembly method comprising the steps of:
    fabricating an elongated flex circuit having a component side, an opposite side and a plurality of foldable portions;
    creating a plurality of traces on said component side substantially excluding said plurality of foldable portions;
    creating a conductive layer on said opposite side substantially including said plurality of foldable portions;
    mounting a detector and an emitter to said component side, said traces providing electrical connections for said detector and said emitter; and
    disposing said plurality of foldable portions around said detector so as to shield said detector from electromagnetic interference.

5. The optical sensor assembly method according to claim 4 wherein said step of fabricating the plurality of foldable portions step comprises the substep of forming a back flap and a plurality of side flaps.

6. The optical sensor assembly method according to claim 5 wherein said disposing step comprises the substeps of adhering said plurality of side flaps to first portions of said detector and adhering said back flap to second portions of said detector.

7. The optical sensor assembly method according to claim 4 further comprising the step of creating a conductive grid portion of at least one of said traces.

8. The optical sensor assembly method according to claim 7 wherein said mounting step comprises the substep of positioning said detector proximate said grid portion so as to shield said detector from electromagnetic interference.

9. A noninvasive disposable optical sensor which outputs a signal usable to determine one or more physiological parameters, the optical sensor comprising:

at least one emitter;

a light sensitive detector capable of detecting light emitted from the at least one emitter and attenuated by body tissue, said detector also capable of outputting a signal usable to determine one or more physiological parameters of the body tissue;

a flexible circuit comprising the at least one emitter, the detector, an interconnect layer, and a substrate layer, wherein the substrate layer is formed from a unitary structure including a plurality of foldable portions extending from a main body portion, and wherein the foldable portions fold over and around the detector while the main body portion substantially covers the interconnect layer, thereby substantially enclosing and shielding the light sensitive detector from external noise; and adhesive attachment wraps capable of adhering the disposable optical sensor to the body tissue, wherein the plurality of foldable portions of the flexible circuit are different from the adhesive attachment wraps and wherein the plurality of foldable portions are not used for attachment of the disposable optical sensor to the body tissue.

10. The optical sensor of claim 9, wherein the disposable optical sensor is part of a patient monitoring system including a patient monitor capable of receiving the signal from the disposable optical sensor and determining the one or more physiological parameters.

11. A method of assembling a multi-layer optical sensor comprising:

fabricating a multi-layer circuit panel including a trace layer and at least one of a top ink layer and a bottom ink layer, wherein the trace layer comprises a plurality of conductive traces;

separating the multi-layer circuit panel into a plurality of multi-layer elongated flexible circuits, wherein each flexible circuit includes a plurality of foldable portions substantially free of the plurality of conductive traces;

mounting a detector and at least one emitter to each flexible circuit, wherein the conductive traces provide electrical connections for each detector and each emitter;

disposing the foldable portions around each detector so as to shield each detector from electromagnetic interference;

attaching sensor panel material to the flexible circuits; and shaping the sensor panel material into multi-layer optical sensors, wherein the shapes assist in attachment of each optical sensor to a measurement site.

12. The method according to claim 11, further comprising the multi-layer circuit panel including the other of the top ink layer and the bottom ink layer.

* * * * *